United States Patent [19]

Goede et al.

[11] Patent Number: 5,503,845
[45] Date of Patent: Apr. 2, 1996

US005503845A

[54] TABLETS, GRANULATES AND PELLETS WITH A HIGH ACTIVE SUBSTANCE CONTENT FOR HIGHLY CONCENTRATED, SOLID DOSAGE FORMS

[75] Inventors: Joachim Goede, Hanau; Jürgen Engel, Alzenau; Helmut Hettche, Dietzenbach, all of Germany

[73] Assignee: ASTA Medica Aktiengesellschaft, Frankfurt am Main, Germany

[21] Appl. No.: 285,145

[22] Filed: Aug. 3, 1994

Related U.S. Application Data

[62] Division of Ser. No. 25,053, Mar. 2, 1993, Pat. No. 5,376,382.

[30] Foreign Application Priority Data

Mar. 11, 1992 [DE] Germany .................. 42 07 717.6

[51] Int. Cl.$^6$ .............................. A61K 9/16; A61K 9/20
[52] U.S. Cl. .................... 424/464; 424/465; 424/489
[58] Field of Search ................... 424/464, 465, 424/489

[56] References Cited

U.S. PATENT DOCUMENTS 5,085,869  2/1992  Olthoff et al. .................. 424/499
5,376,382  12/1994  Goede et al. .................. 424/464

*Primary Examiner*—Thurman K. Page
*Assistant Examiner*—James M. Spear
*Attorney, Agent, or Firm*—Cushman Darby & Cushman

[57] ABSTRACT

A solid medicinal form having an active substance content of over 45 weight % and a process for its preparation by granulating with large amounts of water, drying and optionally conventional tableting and/or pelleting.

13 Claims, No Drawings

TABLETS, GRANULATES AND PELLETS WITH A HIGH ACTIVE SUBSTANCE CONTENT FOR HIGHLY CONCENTRATED, SOLID DOSAGE FORMS

This application is a Division of Ser. No. 08/025,053 filed Mar. 2, 1993, now U.S. Pat. No. 5,376,382.

The present invention relates to a medicinal formulation in tablet form or granulated or in pellet form containing, for example, thioctic acid, flupirtine or mesna in granulated or pelletized form, and optionally pharmaceutically acceptable auxiliary substances.

BACKGROUND OF THE INVENTION

Chemically speaking, thioctic acid (alpha-lipoic acid) is a 1,2-dithiacyclopentane-3-valeric acid. The present invention relates to the racemic form, and also to the pure (R)- or (S)-thioctic acid as well as to mixtures of (R)- and (S)-thioctic acid of any composition. Thioctic acid is a constituent of cell metabolism and is therefore found in many plants and animal organisms. It acts as one of the coenzymes in the oxidative decarboxylation of pyruvate and other alpha-ketoacids. Thioctic acid has been used for a long time in treating various disorders, such as in liver disorders, in liver damage due to mushroom poisoning and in diabetic and alcoholic polyneuropathy, a change in the peripheral nerves associated with metabolic disorders.

Current,. commercially available thioctic acid are tablet formulations which contain a maximum of 200 mg thioctic acid in a tablet weighing 515 mg.

To simplify intake and to increase patient acceptance (compliance), there is a need for thioctic acid tablets in higher concentration and smaller size.

Chemically speaking, mesna is the sodium salt of mercaptoethanesulfonic acid. Mesna is used as a mucolytic agent and to prevent bladder toxicity and nephrotoxicity in treatments involving cytostatic agents of the oxazaphosphorin type. In addition to the sodium salt, it is also possible to use the arginine salt described in European Patent EP 198 542.

Flupirtine is used in the form of the maleate to combat pain. Apart from the maleate, it is also possible to use the hydrochloride, the sulphate, the mandelate as well as other pharmaceutically acceptable salts.

The proportional multiplication of the constituents in a tablet containing 200 mg thioctic acid leads, in active ingredient dosages of more than 500 mg per tablet, to tablets having intrinsic weights of more than 1.2 g. Because of their size it is difficult to swallow tablets of such high intrinsic weight, which leads to their poorer acceptance by patients. It would be desirable to reduce the proportion of auxiliary substance in the higher dosed solid medicinal form.

It is, however, impossible to manufacture thioctic acid-containing, mesna-containing or flupirtine-containing tablets with a reduced proportion of active ingredient which are nevertheless of a satisfactory quality, using conventional manufacturing methods.

For example, higher concentrations of thioctic acid lead to tablet pressing problems. The materials to be pressed tend to adhere to the pressing tools. In addition, cracks appear in the tablets parallel to their surface. In the case of biconvex tablets, the domed surface (lid) tends to break away.

These faults are caused by the properties of thioctic acid, the low melting point of the substance of 60.5° C. (R, S-thioctic acid) and 47° C. (R-thioctic acid) and 46° C. (S-thioctic acid) being particularly critical.

The same problems occur when attempts are made to prepare highly concentrated mesna or flupirtine maleate tablets. Tableting defects occur in the case of these active substances, such as adhesion and crack formation when the active ingredient content in the mass to be pressed exceeds 45 weight %. Adhesion to, and smearing of, the pelleting machines are the main problems during pelleting. In addition, pellet masses moistened in conventional manner with conventional auxiliary substances are not bound sufficiently after the finished pellets have been dried.

Published European Patent Application EP-A 420 042 describes the preparation of solid medicinal forms with a high verapamil hydrochloride content through granulation with a small amount of water, the water content being between 2 and 10 weight % in relation to verapamil hydrochloride. Also, in the compulsory second granulation step of the process, the water content is between 2 and 10 weight %.

SUMMARY OF THE INVENTION

It is therefore an object of the present invention to provide formulations which contain a high proportion of active ingredient, and which can easily be pressed into tablets. A further object of the invention is to overcome the unfavorable technical problems arising from the pressing of for example thioctic acid, mesna or flupirtine, which become increasingly pronounced with increasing active substance concentration.

Reduction in the proportion of auxiliary substances, such as for example to lactose, in the tablet also reduces the probability of signs of intolerance [See, Deutsche Apothekerzeitung 131, 1569 (1991)].

This object is achieved by specially intensive granulation of the active substances together with large amounts of binding agent solutions or by granulation of an active substance binding agent mixture with large amounts of water.

In addition to these two constituents, the granulate may also contain conventional tableting auxiliary substances such as filling, disintegrating and wetting agents. The tablet may also contain additional filling, binding, disintegrating, wetting, flow-promoting, lubricating and antiadhesive agents apart from the granulate.

Surprisingly it has been found that, by intensively moistening the mass to be granulated, is possible to overcome the technologically unfavorable characteristics of thioctic acid and the active substances mesna and flupirtine.

The medicinal formulations of the invention contain between 45 weight % and 100 weight % of active ingredient, preferably between 75 weight% and 100 weight % and, particularly preferred, between 85 weight % and 100 weight %. Related to the prepared amount of solid active ingredient, at least 30 weight %, preferably 40–100 weight %, in particular 50–70 weight % of water or aqueous binding agent solutions are used. Conventional granulation processes operate with a maximum of 30 weight % of water (*Der Pharma-Werker*, Editis Cantor, 1970, page 72–74; *Hager Handbuch der pharm. Praxis*, 4th Edition 1971, Volume 7 a, page 712) as granulating liquid or solvent for the binding agent. In the case of thioctic acid a maximum of 15 weight % of water have hitherto been used as granulating liquid.

Page 86 of List, *Arzneiformenlehre*, Stuttgart (1985), describes the moisture content of the mass to be granulated as follows:

It is generally found that a mass has the correct moisture content if it forms a ball when compressed in the hand and does not immediately fall apart again when released, but can be easily rubbed between the fingers without smearing". Page 158 of Voigt, *Lehrbuch der pharmazeutischen Technologie*, Weinheim (1987) describes the degree of moisture of the granulate as being "earth moist". Moistening agents that can be used are alcohols with 1–4 carbon atoms, esters of lower organic acids and lower organic alcohols with a total of up to 6 carbon atoms, for example methanol, ethanol, isopropanol, acetic acid ethyl ester and, particularly preferred, water.

Binding agents useful with the invention can be any conventional pharmaceutically acceptable binding agents such as cellulose derivatives (for example ethyl cellulose, hydroxyethyl cellulose, carboxymethyl cellulose, methyl cellulose, hydroxypropylmethyl cellulose), gelatin, starch, polyglycols (mean molecular weight 1000–35000 Dalton), polyvinyl alcohols, polyvinyl pyrrolidone, polyacrylic acid, vinyl pyrrolidone-vinyl acetate copolymer, alginates, saccharose or glucose, polysaccharides such as, for example natural rubbers such as, for example, gum arabic, tragacanth, pectin, guar-rubber in amounts of 1–30 weight %, preferably 5–20 weight %, in particular 10–15 weight %, relative to the weight of active ingredient(s)(concentration of the aqueous binding agent solutions 2–30 weight %, preferably 5–15 weight %).

It also is possible to simultaneously use various binding agents, for example different cellulose derivatives, in association with each other. The binding agents can be worked into the dry powder mixture or incorporated after having been dissolved or dispersed in the granulating liquid. It also is suitable to use both dry binding agent, mixed with the active ingredient, together with binding agent dissolved or dispersed in the granulating liquid.

The moist mass is intensively worked mechanically in the conventional manner used for granulation in order to obtain even moistening and compaction of the mass. This is effected for example in a high performance granulator. These machines have a mixer arm rotating about a vertical axis and a cutter rotating at higher speed either vertically or in parallel to the mixer arm axis. (Examples of such machines are: Diosna pharma mixer, series P, Lödige ploughshare mixer FM with knife-head fittings, Colette or Fielder-mixer-granulator). Granulation occurs with maximum energy input, i.e. in each case at the highest speed of revolution of the mixer paddles and choppers and, depending on the granulator, lasts 5–20 minutes. The consistency of the granulate can be described as being pasty, but without a visibly separated liquid phase. In contradistinction thereto, when they have the previously obtained optimum moisture content, conventional granulates are described as being of snowball-like consistency. If required, the moist mass is passed through a strainer having a ring matrix (for example Alexanderwerk-Reibschnitzler, Stephan granulating machine, Nica extruder) or a granulating sieve and further compacted in this manner. Particularly high compaction produces pellet-like products. Pellets can be defined as being spherical or cylindrical particles with a diameter of 0.1 to about 5 mm. Pellets of this kind can be rounded and flattened before drying on a rotating corrugated disc (for example in a Nica spheronizer).

The granulate or the pellets are subsequently dried in a fluidized air bed or on hurdles in the conventional manner up to a final moisture of under 10, preferably under 6 weight % and in particular under 3 weight % (related to the solid matter weight). This granulation is optionally repeated with more than 15 weight %, preferably 30–70 weight %, in particular 40–50 weight % of water or aqueous binding agent solutions in order to increase the compaction of the granulate and the binding within the granulate grains.

The binding agent content is 2–30 weight %, preferably 5–15 weight %, relative to the amount of solvent used.

If necessary the granulate or the pellets are subsequently mixed with filling, binding, disintegrating, wetting, flow-promoting, lubricating and/or anti-adhesion agents. Filling agents that may for example be used are: cellulose, cellulose derivatives, saccharose, lactose, glucose, fructose, calcium phosphates, calcium sulphates, calcium carbonates, starch, modified starch, sugar alcohols such as sorbitol or mannitol.

Binding agents that are suitable are, for example, cellulose derivatives (for example ethyl cellulose, methyl cellulose, hydroxyethyl cellulose, carboxymethyl cellulose, hydroxypropylmethyl cellulose), gelatin, starch, modified starch, polyglycols (mean molecular weight 1000–35000 Dalton), polyvinyl alcohols, polyvinyl pyrrolidone, polyacrylic acid, vinyl pyrrolidone-vinyl acetate copolymers, alginates, saccharose, glucose, polysaccharides. Disintegrants that may for example be used are: starch, modified starch, cellulose, cellulose derivatives, alginates or cross-linked polyvinyl pyrrolidone.

Wetting agents that may, for example, be used are: sodiumdioctyl sulfosuccinate, sodiumlauryl sulphate, polysorbates or polyoxyethylene stearic acid esters. Flow-promoting agents that may be used are, for example, colloidal silicon dioxide, talcum or magnesium stearate. Lubricants that may, for example, be used are: magnesium stearate, calcium stearate, D,L-leucine, talcum, stearic acid, polyglycols (mean molecular mass 3000–35000), fatty alcohols or waxes.

Anti-adhesion agents (lubricants) that may, for example, be used are: starch, talcum, magnesium stearate, calcium stearate or D,L-leucine.

The mixture prepared in this way is pressed into tablets in conventional manner. In so doing it may be of advantage to reduce the temperature of the mass to be pressed to below room temperature before pressing. The temperature of the mass to be pressed can be 0° C.–30° C., preferably 5° C.–20° C., in particular 8° C.–15° C.

The pellets are either pressed into tablets or filled into hard gelatin capsules or bags.

The intensive mechanical processing and large amount of granulating liquid used are characterizing and decisive for the process. Precooling of the mass to be pressed (24 hours at +8° C.) further improves the pressing characteristics of the tablet mass.

DETAILED DESCRIPTION OF PREFERRED EMBODIMENTS

The invention is illustrated by the following examples.

EXAMPLE 1

Granulate containing 300 mg thioctic acid for each 318 mg of granulate

Corn starch is processed to form corn starch paste in the conventional manner (List *Arzneiformenlehre*, Stuttgart (1985), page 88).

1500 g thioctic acid are moistened with 880 g of a 10% aqueous corn starch paste in a Diosna P10 mixer granulator for 10 minutes (maximum energy input: mixer 433 rpm, chopper 3000 rpm). The resulting moist mass is passed through a sieve which has a 2 mm mesh size and spread on drying hurdles in a circulating air drying cabinet with an air inlet temperature of 40° C. to a relative moisture of 25–30%. The dry granulate is passed through a sieve of mesh size 0.8 mm. The granulate may optionally be provided with a gastric juice-soluble, gastric juice-permeable or gastric juice-insoluble coating and filled into capsules or bags.

EXAMPLE 2

Tablets containing 300 mg thioctic acid and having a 319 mg tablet weight 1588 g of the granulate of Example 1 are mixed with 6 g magnesium stearate and pressed into biconvex tablets with a weight of 319 mg, a diameter of 10 mm and a radius of curvature of 8 mm. The tablets are smooth, shiny and without cracks. The pressing tools are free of traces of adhering tablet mass.

The tablets disintegrate within 2 minutes in the disintegration tester of DAB 9 (test liquid: water, 37° C.).

It is optionally possible to provide the tablets with a gastric juice-soluble or gastric juice-resistant film coating using conventional methods.

EXAMPLE 3

Granulate with 300 mg thioctic acid for each 330 mg granulate 1500 g thioctic acid are mixed with 150 g hydroxypropyl cellulose. The mixture is moistened with 900 g purified water in a Diosna P10 mixer granulator for 12 minutes (maximum energy input: mixer 433 rpm, chopper level 3000 rpm).

The moist mass is passed through a granulating machine (Stephan KG-150P) with a ring cylinder, aperture size 2 mm. The moist granulate is dried in a fluidized air bed dryer (Glatt WSG 3/5) to an air inlet temperature of 30–40° C. at a relative moisture of 25–30%. The dried granulate is passed through a sieve of mesh size 0.8 mm.

The granulate can be filled into capsules or bags.

EXAMPLE 4

Tablets with 300 mg thioctic acid and a 331 mg tablet weight 1650 g of the granulate of Example 3 are mixed with 6 g magnesium stearate and pressed into oblong tablets having a weight of 331 mg and the dimensions 13×6 mm, radius of curvature 4.5 mm. The tablets are smooth, shiny and without cracks and contain 300 mg thioctic acid. The pressing tools are free of adhering tablet mass.

The tablets disintegrate within 2 minutes in the disintegration tester of DAB 9 (test liquid: water, 37° C.

It is optionally possible to provide the tablets with a gastric juice-permeable, gastric juice-soluble or gastric juice-resistant film coating using conventional methods.

EXAMPLE 5

Granulate with 800 mg thioctic acid for each 825 mg granulate 1800 g thioctic acid are mixed with 720 g of a 5% gelatin solution in a Diosna P10 mixer granulator for 15 minutes (mixer 433 rpm, chopper 3000 rpm). The moist mass is passed through a sieve of mesh size 3.15 mm and dried in a fluidized air bed dryer (Glatt WSG 3/5) at an air inlet temperature of 30°–35° C. to a relative moisture of 30–35%. The dried granulate is passed through a sieve of mesh size 1.0 mm. The dry granulate is then mixed with 432 g of a 5% gelatin solution in a Diosna P10 mixer granulator for 10 minutes (mixer 433 rpm, chopper 3000 rpm). The moist mass is dried in a fluidized air bed dryer (Glatt WSG 3/5) at an inlet temperature of 25°–35° C. up to a relative moisture of 30–35%. The dry granulate is passed through a sieve of mesh size 1.25 mm. The granulate can be filled into capsules or bags.

EXAMPLE 6

Tablets with 800 mg thioctic acid and an 835 mg tablet weight 1858 g of the granulate of Example 5 are mixed with 20 g magnesium stearate and pressed to oblong tablets, size 18×8 mm, weight 835 m. The tablets are smooth, shiny and without cracks and contain 800 mg thioctic acid. The pressing tools are free of adhering tablet mass, even towards the end of the pressing process. The tablets disintegrate within 3–5 minutes in the disintegrating tester of DAB 9 (test liquid: water, 37° C.

COMPARATIVE EXAMPLE 7

Tablets with 300 mg thioctic acid and a 331 mg tablet weight 1500 g thioctic acid are mixed with 150 g hydroxypropyl cellulose. The mixture is mixed with 250 g purified water in a Diosna P10 mixer granulator for 3 minutes (mixer 215 rpm, without chopper, then for 2 minutes with the mixer at 215 rpm, chopper at 1500 rpm).

The earth-moist mass is passed through a granulating machine (Stephan KG-150P) with a ring cylinder, aperture size 2 mm. The moist granulate is dried in a fluidized air bed dryer (Glatt WSG 3/5) at an air inlet temperature of 30°–40° C. to a relative moisture of 25–30%. The dry granulate is passed through a sieve of mesh size 0.8 mm, homogeneously mixed with 6 g magnesium stearate and pressed on an eccentric or rotary press into oblong tablets with a weight of 331 mg and the dimensions 13×6 mm, radius of curvature 4.5 mm. The tablets adhere to the pressing tools after only a few tablets have been pressed, fail to detach themselves completely from the pressing tools when ejected from the machine and express capping or display elongated cracks at the edge.

EXAMPLE 8

Example of high dosage flupirtine tablets 1500 g flupirtine maleate are mixed with 150 g hydroxypropyl cellulose (L-HPC LH22). 1500 g purified water are added to this powder mixture and mixed in an intensive mixer, Diosna P 25 with maximum energy input for 15 minutes (mixer 350 rpm, chopper 3000 rpm). The moist mass is predried on hurdles in a circulating air drying cabinet for 30 minutes at 60° C. and passed through a sieve of mesh size 3.15 mm. The granulate is dried in a circulating air drying cabinet at 50° C. to a relative moisture of 30–35% and passed through a sieve of mesh size 1.0 mm. After adding 16.5 g magnesium stearate to the sieved granulate the resulting mixture is mixed in a Turbula mixer, T10B for 2 minutes at 30 rpm. The mixture is pressed into biplanar tablets with a diameter of 9 mm and a weight of 143 mg. The mass can be pressed easily and without adhering to the pressing tools.

The tablets are smooth, slightly shiny and without cracks. They disintegrate in less than one minute in the disintegration tester of DAB9 (test liquid: water, 37° C.).

EXAMPLE 9 FOR HIGH DOSAGE MESNA TABLETS

Tablets with 300 mg mesna for each 322 mg tablet weight 416 g corn starch are processed into corn starch paste with 2080 g water in the conventional manner.

6000 g mesna are mixed with this corn starch paste in an intensive mixer, Diosna P 25 with maximum energy input for 12 minutes (mixer 350 rpm, chopper 3000 rpm). The moist mass is pre-dried for 10 minutes at 50° C. on hurdles in a circulating air drying cabinet and then passed through a sieve of mesh size 3.15 mm. After further drying for eight hours at 50° C. in a circulating air drying cabinet the granulate is passed through a sieve of mesh size 0.8 mm. After adding 13 g magnesium stearate to the sieved granulate, the resulting mixture is mixed in a Turbula mixer, T10B for 5 minutes at 30 rpm. The mixture is pressed into tablets with a diameter of 9 mm, radius of curvature of 12.5 mm and a weight of 322 mg. No pressing mass adheres to the pressing tools and no coating forms, even after the machine has been running for a considerable length of time. The tablets are smooth, slightly shiny and without cracks. They disintegrate within 5–7 minutes in the disintegrating tester of DAB9 (test liquid: water, 37° C.).

What is claimed is:

1. A medicinal formulation in the form of tablets, granulates or pellets containing an active ingredient selected from the group consisting of mesna and flupirtine maleate, and having an active ingredient content of more than 45% by weight, said granulate or the granulate used to produce said tablets being produced by intensive moistening of said active ingredient with more than 30 weight % water, relative to the amount of solid substance used, the active ingredient being repeatedly moistened with maximum energy input in a qranulator, and subsequently dried at a temperature between 20° C. and 50° C.

2. A medicinal formulation in the form of tablets, granulates or pellets as set forth in claim 1 in which the active ingredient content is more than 75 weight %.

3. A medicinal formulation in the form of tablets, granulates or pellets as set forth in claim 2 in which the active ingredient content is more than 85 weight %.

4. A process for the preparation of granulate or pellets which comprises granulating or pelleting at least one pharmaceutically active ingredient or a mixture of at least one active ingredient and at least one auxiliary substance with more than 30 weight % of water, relative to the amount of solid substances used, with maximum energy input, wherein the active ingredient or ingredients are selected from the group consisting of mesna and flupirtine maleate.

5. A medicinal formulation in the form of tablets, granulates or pellets containing mesna, said granulate or the granulate used to produce the tablets being produced by intensive moistening of mesna with more than 30 weight % water, relative to the amount of solid substances used.

6. A medicinal formulation in the form of tablets, granulates or pellets containing the maleate of 2-amino-3-ethoxycarbonyl-amino-6-(4-fluoro)-benzylamino ridine, said granulate or the granulate used to produce the tablets being produced by intensive moistening of the maleate of 2-amino-3-ethoxycarbonyl-amino-6-(4-fluoro)-benzylamino pyridine with more than 30 weight % water, relative to the amount of solid substances used.

7. A process for the preparation of a medicinal formulation as set forth in any one of claims 1–3 which comprises repeatedly moistening the active ingredient, with maximum energy input in a granulator with more than 15 weight % water, and subsequently drying at temperatures between 20° C. and 50° C.

8. A process as set forth in claim 7 including processing the granulate into pellets or tablets.

9. A process as set forth in claim 4 including the step of converting the granulate or pellets thus obtained into tablets.

10. A process according to claim 7 in which the active ingredient is mesna.

11. A process according to claim 7 in which the active ingredient is flupirtine maleate.

12. A process as set forth in claim 7 in which the amount of water is more than 30 weight %.

13. A medicinal formulation in the form of granulate bodies or pellets produced by a process in which the active ingredient or the mixture of active ingredients and auxiliary substances are granulated at least once with more than 30 weight % water relative to the dry weight of the solid substance and with maximum energy input in a granulator and subsequently dried at a temperature between 20° C. and 50° C., wherein the active ingredient or ingredients are selected from the group consisting of mesna and flupirtine maleate.

* * * * *